United States Patent [19]

Grolig et al.

[11] 4,009,216
[45] Feb. 22, 1977

[54] PREPARATION OF ISOPROPYL CHLORIDE

[75] Inventors: Johann Grolig, Leverkusen;
Manfred Martin, Cologne; Gerhard Scharfe, Leverkusen, all of Germany

[73] Assignee: Bayer Aktiengesellschaft, Leverkusen, Germany

[22] Filed: Apr. 16, 1975

[21] Appl. No.: 568,641

Related U.S. Application Data

[63] Continuation-in-part of Ser. No. 418,142, Nov. 21, 1973, abandoned.

[30] Foreign Application Priority Data

Dec. 9, 1972   Germany ........................ 2260336

[52] U.S. Cl. ............................................. 260/663
[51] Int. Cl.$^2$ ....................................... C07C 17/08
[58] Field of Search ................................... 260/663

[56] References Cited

UNITED STATES PATENTS 2,033,374   3/1936   Gayey ............................... 260/663

*Primary Examiner*—D. Horwitz
*Attorney, Agent, or Firm*—Burgess, Dinklage & Sprung

[57] ABSTRACT

In the preparation of isopropyl chloride wherein propylene and hydrogen chloride are reacted at elevated temperature in the gaseous phase in the presence of aluminum oxide as catalyst, the improvement which comprises effecting the reaction at a pressure of about 3 to 8 atm, at a temperature of about 50° to 200° C and in the presence of aluminum oxide having an internal surface area of about 200 to 500 m$^2$/g.

6 Claims, No Drawings

PREPARATION OF ISOPROPYL CHLORIDE

This application is a continuation-in-part of application Ser. No. 418,142, filed Nov. 21, 1973, now abandoned.

This application relates to the preparation of isopropyl chloride by the reaction of propylene with hydrogen chloride.

German Pat. No. 509,263 discloses preparing isopropyl chloride in the liquid phase through the reaction of isopropanol with aqueous hydrochloric acid. This process has the disadvantage that corrosion problems are created by the use of aqueous hydrochloric acid. Furthermore, it uses relatively expensive raw materials.

Chemical Engineering Progress, Vol. 48, No. 11, pp 564 to 569, 1952 discloses preparing isopropyl chloride through the reaction of propylene and hydrogen chloride in the gaseous phase in the presence of aluminum oxide as catalyst. As stated by the author at page 565, column 1, lines 30 to 37:

"At temperatures of operation over 100° C, the catalyst became coated with a deposit that varied in color from orange to black, and the activity of the catalyst decreased rapidly. Although considerable effort was expended in trying to achieve a constant catalyst activity, this was never achieved."

Gayer in U.S. Pat. No. 2,033,374 discloses reacting propylene and hydrogen chloride over alumina at elevated temperature.

It is accordingly an object of the present invention to provide a process for the preparation of isopropyl chloride at high rates of conversion.

This and other objects and advantages are realized in accordance with the present invention which relates to an improvement in the preparation of isopropyl chloride through the reaction of propylene and hydrogen chloride at elevated temperature in the gaseous phase in the presence of aluminum oxide as catalyst. In accordance with the invention the reaction is performed at a pressure of about 3 to 8 atm, at a temperature of about 50° to 200° C, and in the presence of aluminum oxide having an internal surface area of about 200 to 500 m²/g. The method of the invention is distinguished by the fact that loss of catalyst activity is virtually eliminated.

A suitable catalyst is aluminum oxide having an internal surface area according to BET (Bunauer, Emmet and Teller, Journal of American Chemical Society 60, p. 309, 1938) of about 200 to about 500 m²/g. Preferably an aluminum oxide with an internal surface area of about 300 to 400 m²/g (according to BET) is used. It is advantageous to use aluminum oxide of a purity of more than about 99 wt-%, e.g., with a purity of more than about 99.5 wt-% or more than about 99.8 wt-%. It is furthermore advantageous to use catalysts whose $SiO_2$ content is smaller than about 1 wt-%, for example smaller than about 0.3 wt-% or smaller than about 0.1 wt-%.

The catalyst may be present in various forms, e.g., in powder form, in coarse granular form or in the form of spherules. Suitable grain sizes, when the catalyst is in powder form, are for example about 0.01 to 1 mm. If the catalyst is present in coarsely granular form or in the form of spherules, grain sizes of about 3 to 7 mm, e.g., about 4 to 6 mm, are suitable. The catalyst may be fixedly arranged in reaction tubes when it is in coarse granular or spherical form. Suitable reaction tube diameters are about 20 to 50 mm, e.g., about 25 to 30 mm. Suitable reaction tube lengths are about 2 to 10 m, e.g., about 4 to 6 m.

The reaction is performed at temperatues of about 50° to 200° C, especially about 100° to 150° C. within the pressure range from about 3 to 8 atm, the process of the invention is performed preferably at pressures of about 4 to 7, e.g., about 5 to 6 atm.

The hydrogen chloride may be in common commercial form. Advantageously, hydrogen chloride in anhydrous form is used. The propylene may be used in pure form or in a mixture with other hydrocarbons such as propane and/or ethane. The ratio of propylene to hydrogen chloride may vary within wide limits, as for example about 5:1 to 1:5 moles. The reaction may also be performed at molar ratios of about 2:1 to 1:2 or in approximately the stoichiometric ratio of 1 mole hydrogen chloride per mole of propylene. The process of the invention permits the reaction to be performed with high space-time yields, e.g., with space-time yields of about 100 to 1000 g of isopropyl chloride per liter of catalyst per hour. In general it is performed with space-time yields of about 300 to 600 g of isopropyl chloride per liter of catalyst per hour. The conversion in a single straight-through pass may vary within wide limits, e.g. about 60 to 100%. In general, the process of the invention is so conducted that high conversions of about 80 to 95%, for example, are established in the straight-through passage.

The gaseous reaction product may be cooled down, for example to temperatures below about 50° C, preferably about 0° to 50° C, and especially preferably about 30° to 40° C. The cooling is advantageously performed under pressure. Thus the gaseous reaction product may be separated into a gaseous phase and a liquid phase consisting essentially of isopropyl chloride. Dissolved gases such as propylene, hydrogen chloride and in some cases other hydrocarbons, may be separated from the liquid phase, for example by distillation under the reaction pressure, and pure isopropyl chloride obtained at the sump of the column. The gaseous components driven off in the distillation column and the gas phase which is produced upon cooling may be returned to the reaction. If a propylene containing additional hydrocarbons is used, these hydrocarbons are concentrated by the recycling. An excessively great increase of the hydrocarbon content in the recycled gas may be prevented by side stream removal.

The reaction may be performed in the presence of inerts, such as nitrogen, noble gases and/or carbon dioxide. It is advantageous to perform the reaction in the absence of oxygen.

The process of the invention is distinguished by the fact that an inexpensive and easily available hydrocarbon is used as the starting product. Owing to the use of gaseous hydrogen chloride virtually no corrosion problems occur. High space-time yields of isopropyl chloride are obtained by the method of the invention, and no reduction of catalyst activity can be observed even after more than 1000 hours of operating time. Even with highly active catalysts such as those having internal surface areas of 200 to 500 m²/g, unexpectedly it has been found that a pressure of 3 to 8 atmospheres is an important factor in prolonging catalyst life and in maintaining a substantially constant level of catalytic activity over long periods of time. Therefore the efficiency of the process using these pressures remains high.

By the method of the invention isopropyl chloride can be prepared which is suitable as a solvent and extractant for fats and oils (Angewandte Chemie 62, p. 23, 1950).

The invention will be further described in the following illustrative example wherein all parts are by weight unless otherwise expressed.

EXAMPLE

A reaction tube of 2 m length and an inside diameter of 25 mm was filled with 900 ml of a catalyst in the form of 5 mm beads. The catalyst consisted of aluminum oxide in a purity of more than 99.5 wt-%; the $SiO_2$ content amounted to 0.02 wt-%. The internal surface area of the catalyst amounted to 320 $m^2/g$ (according to BET). Hydrogen chloride and a technical propylene fraction with a content of 93 mole-% propylene and 7 mole-% propane were passed through the catalyst at 125° C and a pressure of 6 atm. The gaseous reaction product was cooled to 40° C under the reaction pressure and separated into a liquid and a gaseous phase. The gaseous phase was recycled into the reaction. The liquid phase was freed of gaseous components (propane, propylene and hydrogen chloride) in a distillation column operated under pressure. Pure isopropyl chloride was taken from the sump of the column.

The gases produced at the head of the column, consisting of propylene, propane, hydrogen chloride and isopropyl chloride, were recycled into the reaction. A side stream containing propane and propylene in a ratio of about 1:1 was taken from the circulating gas in order to avoid a build-up of propane in the circuit. The following amounts of starting product were passed through the catalyst (given in moles per liter of catalyst per hour): hydrogen chloride 7.2, propylene 7.1, propane 0.3. The results of the run are given in the following table.

| Hours of Operation | Volume-time yield in g of isopropyl chloride per liter of catalyst per hour |
|---|---|
| 100 | 550 |
| 200 | 530 |
| 300 | 530 |
| 400 | 530 |
| 500 | 530 |
| 600 | 530 |
| 700 | 530 |
| 800 | 530 |
| 900 | 530 |
| 1000 | 530 |

After the start-up period the catalyst had a constant activity in the period from 200 to 1000 hours.

In the foregoing specification and the following claims the recited pressures are all absolute values.

It will be appreciated that the instant specification and examples are set forth by way of illustration and not limitation, and that various modifications and changes may be made without departing from the spirit and scope of the present invention.

What is claimed is:

1. In the preparation of isopropyl chloride wherein propylene and hydrogen chloride are reacted at elevated temperature in the gaseous phase in the presence of aluminum oxide as catalyst, the improvement which comprises effecting the reaction at a pressure of about 3 to 8 atm, at a temperature of about 50° to 200° C, and in the presence of aluminum oxide having an internal surface area of about 200 to 500 $m^2/g$.

2. The process of claim 1, wherein the reaction is effected at a pressure of about 4 to 7 atm.

3. The process of claim 1, wherein the reaction is effected at about 100° to 150° C.

4. The process of claim 1, wherein the aluminum oxide has an internal surface area of about 300 to 400 $m^2/g$.

5. The process of claim 1, wherein the catalyst comprises aluminum oxide with a purity of greater than 99 wt-% and a $SiO_2$ content of less than 0.1 wt-%.

6. The process of claim 5, wherein the reaction is effected at about 100° to 150° C under a pressure of about 5 to 6 atm, the aluminum oxide having an internal surface area of about 300 to 400 $m^2/g$.

* * * * *